US011707490B2

(12) United States Patent
Berggren

(10) Patent No.: US 11,707,490 B2
(45) Date of Patent: Jul. 25, 2023

(54) METHODS AND REAGENTS FOR TREATING DIABETES

(71) Applicant: Biocrine AB, Solna (SE)

(72) Inventor: Per Olof Berggren, Solna (SE)

(73) Assignee: BIOCRINE AB

( * ) Notice: Subject to any disclaimer, the term of this patent is extended or adjusted under 35 U.S.C. 154(b) by 915 days.

(21) Appl. No.: 16/512,731

(22) Filed: Jul. 16, 2019

(65) Prior Publication Data

US 2020/0023013 A1 Jan. 23, 2020

Related U.S. Application Data

(60) Provisional application No. 62/700,587, filed on Jul. 19, 2018, provisional application No. 62/700,583, filed on Jul. 19, 2018.

(51) Int. Cl.
| | |
|---|---|
| *C12N 15/09* | (2006.01) |
| *A61K 35/39* | (2015.01) |
| *A61K 9/00* | (2006.01) |
| *C12N 5/071* | (2010.01) |
| *A61P 3/10* | (2006.01) |
| *A61K 48/00* | (2006.01) |

(52) U.S. Cl.
CPC ............ *A61K 35/39* (2013.01); *A61K 9/0019* (2013.01); *A61K 9/0048* (2013.01); *A61K 48/0075* (2013.01); *A61P 3/10* (2018.01); *C12N 5/0676* (2013.01)

(58) Field of Classification Search
CPC .................................................... C12N 15/09
See application file for complete search history.

(56) References Cited

U.S. PATENT DOCUMENTS

| | | | |
|---|---|---|---|
| 9,462,973 B2 | 10/2016 | Berggren | |
| 9,463,205 B2 | 10/2016 | Berggren et al. | |
| 9,702,867 B2 | 7/2017 | Berggren | |
| 10,207,012 B2 | 2/2019 | Berggren et al. | |
| 10,228,364 B2 | 3/2019 | Berggren | |
| 10,338,060 B2 | 7/2019 | Berggren | |
| 2012/0328630 A1 | 12/2012 | Berggren et al. | |
| 2015/0259416 A1 | 9/2015 | Berggren et al. | |
| 2017/0037118 A1 | 2/2017 | Berggren et al. | |

OTHER PUBLICATIONS

Qi, "Transplantation of encapsulated pancreatic islets as a treatment for patients with Type 1 diabetes mellitus," Advances in Medicine, article ID No. 429710, 15 pp., 2014.*
English machine translation of Kiyono et al., JP 4136434 B2, 2008.*
Berggren et al., "Removal of Ca2+ channel B3 subunit enhances Ca2+ oscillation frequency and insulin exocytosis," Cell 119:273-84 (Oct. 2004).

(Continued)

*Primary Examiner* — Rosanne Kosson
(74) *Attorney, Agent, or Firm* — McDonnell Boehnen Hulbert & Berghoff LLP

(57) ABSTRACT

Disclosed are methods for treating or limiting development of diabetes, by transplanting into the eye of a subject with diabetes or at risk of diabetes an amount effective to treat or limit development of diabetes of insulin-producing cells engineered to reduce expression of a β3 subunit of Cav (Cavβ3).

20 Claims, 7 Drawing Sheets

(56) References Cited

OTHER PUBLICATIONS

Lee et al., "Blocking Ca2+ channel B3 subunit reverses diabetes," Poster Presentation Poster P2696, Board No. B853, 2017 ASCB Annual Meeting Abstracts Jan. 2018, one page.
Yang et al., "The role of voltage gated calcium channels in pancreatic B-cell physiology and pathophysiology," Endocrine Reviews 27(6):621-76 (Oct. 2006).
The International Search Report and Written Opinion for International Application No. PCT/EP2019/069108; dated Nov. 4, 2019, pp. 1-16.

\* cited by examiner

A

B

Tx CTL    Tx Ca$_v$β$_3$$^{-/-}$

C

Tx CTL    Tx Ca$_v$β$_3$$^{-/-}$

D

E

METHODS AND REAGENTS FOR TREATING DIABETES

CROSS-REFERENCE

This application claims priority to U.S. Provisional Patent Application Ser. No. 62/700,583 filed Jul. 19, 2018 and U.S. Provisional Patent Application Ser. No. 62/700,587 filed Jul. 19, 2018, each incorporated by reference in its entirety.

BACKGROUND

The International Diabetes Federation (IDF) has estimated that the number of people with diabetes in 2011 was 366 million and this number is expected to grow to 550 million by 2030. The majority of patients are suffering from type-2 diabetes mellitus (T2DM). There is a link between obesity, insulin resistance and the development of T2DM, but the precise underlying mechanisms remain unknown and it becomes paramount to identify potential therapeutic targets that can ultimately address this crucial problem.

Classical target tissues subjective to insulin resistance in T2DM are muscle, liver and fat. These peripheral tissues maintain glucose homeostasis by effectively responding to insulin and failure of insulin to activate its receptors and the downstream signaling cascades result in defect glucose handling. In addition, insulin can stimulate its receptors on the pancreatic β-cell and thereby directly contribute to a positive feedback loop for insulin biosynthesis and secretion.

SUMMARY

In one aspect, the disclosure provides methods for treating or limiting development of diabetes, comprising transplanting into the eye of a subject with diabetes or at risk of diabetes an amount effective to treat or limit development of diabetes of insulin-producing cells engineered to reduce expression of a β3 subunit of Cav (Cavβ3). In one embodiment, the insulin-producing cells are engineered to disrupt each copy of the Cavβ3 gene. In another embodiment, the insulin-producing cells are engineered to reduce expression of apoCIII, such as by disrupting each copy of the apoCIII gene. In another embodiment, the insulin-producing cells are engineered to reduce expression of one or more chemokines, including but not limited to CCL2, CCL3, CCL5, CXCL1, CXCL9, CXCL10, and/or CXCL11, and/or one or more cytokines including but not limited to IL-6 and/or IL-8. In one embodiment, the insulin-producing cells are engineered to reduce expression of one or more major histocompatibility complex (MHC) class I proteins, including but not limited to human HLA-A, HLA-B, and/or HLA-C genes. In a further embodiment, the insulin-producing cells are engineered to disrupt each copy of the one or more MHC class I proteins. In one embodiment, the insulin-producing cells are engineered to increase expression of one or more proteins beneficial to insulin producing cells, including but not limited to GLP1 receptors, insulin receptors, and/or cytokine IL1B. In another embodiment, the insulin-producing cells comprise isolated pancreatic islets or isolated pancreatic β cells, such as isolated human pancreatic islets or isolated human pancreatic β cells. In a further embodiment, the transplantation into the eye involves transplantation into the anterior chamber of the eye, including but not limited to transplantation into the anterior chamber of the eye involves injection through the cornea. In one embodiment, the subject, such as a human subject, has diabetes and the transplanting comprising transplanting into the eye of a subject with diabetes (including but not limited to type 1 and type 2 diabetes) an amount effective to treat diabetes. In another embodiment, the subject, such as a human subject, is at risk of diabetes and the transplanting comprising transplanting into the eye of a subject at risk of diabetes (including but not limited to a risk of type 1 and type 2 diabetes) an amount effective to limit development of diabetes. In a further embodiment, the subject, such as a human subject, overexpresses Cavβ3 compared to a control.

In another aspect, the disclosure provides recombinant cells comprising an insulin-producing cell engineered to reduce expression of a β3 subunit of Cav (Cavβ3). In one embodiment, the insulin-producing cells are engineered to disrupt each copy of the Cavβ3 gene. In another embodiment, the insulin-producing cells are engineered to reduce expression of apoCIII, such as by disrupting each copy of the apoCIII gene. In another embodiment, the insulin-producing cells are engineered to reduce expression of one or more chemokines, including but not limited to CCL2, CCL3, CCL5, CXCL1, CXCL9, CXCL10, and/or CXCL11, and/or one or more cytokines including but not limited to IL-6 and/or IL-8. In one embodiment, the insulin-producing cells are engineered to reduce expression of one or more major histocompatibility complex (MHC) class I proteins, including but not limited to human HLA-A, HLA-B, and/or HLA-C genes. In a further embodiment, the insulin-producing cells are engineered to disrupt each copy of the one or more MHC class I proteins. In one embodiment, the insulin-producing cells are engineered to increase expression of one or more proteins beneficial to insulin producing cells, including but not limited to GLP1 receptors, insulin receptors, and/or cytokine IL1B. In another embodiment, the insulin-producing cells comprise isolated pancreatic islets or isolated pancreatic β cells, such as isolated human pancreatic islets or isolated human pancreatic β cells.

DETAILED DESCRIPTION

Figure 1:
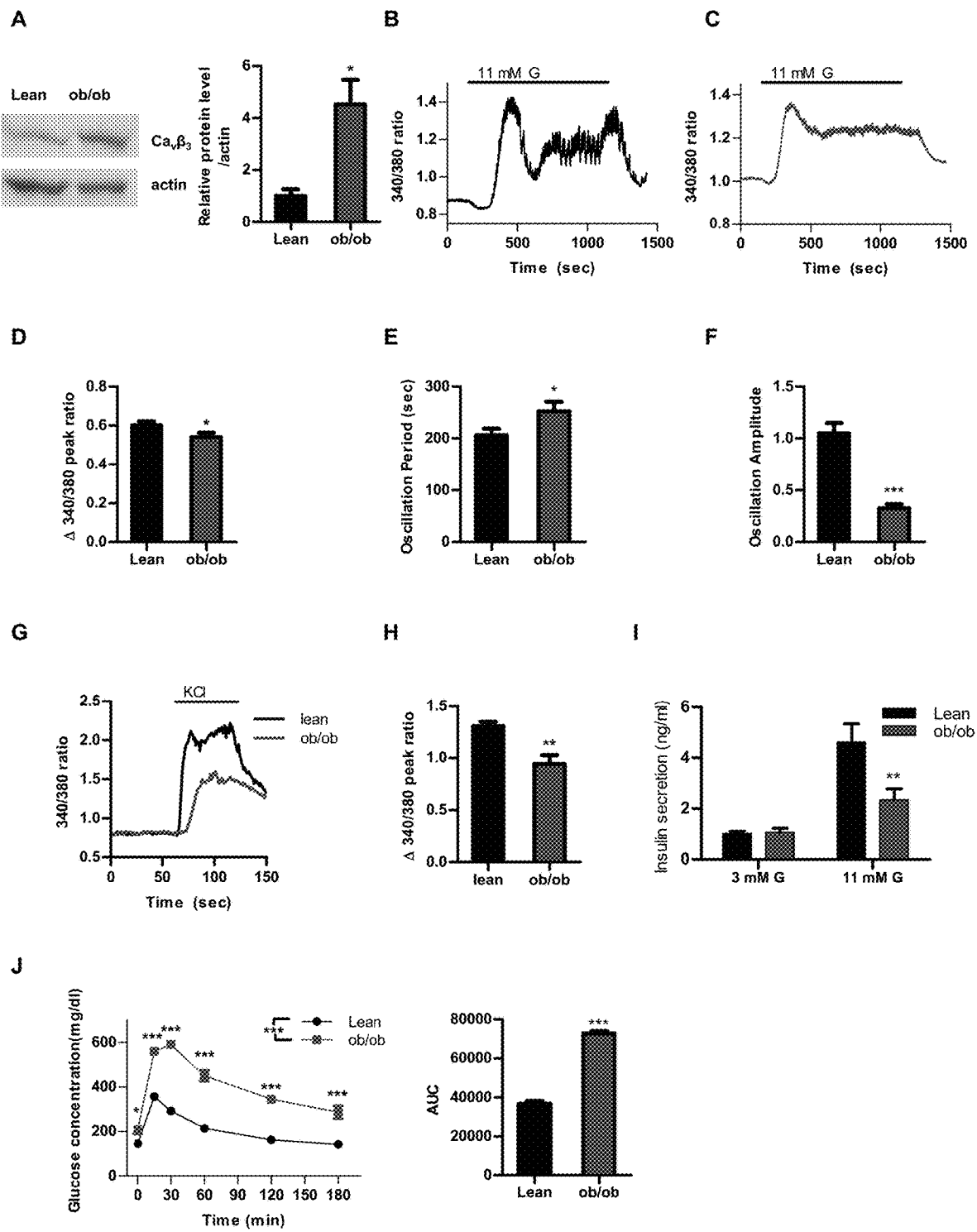
FIG. 1. $Ca_v\beta_3$ expression and $[Ca^{2+}]_i$ dynamics were altered in islets from ob/ob mice. (A) Left panel shows protein levels of $Ca_v\beta_3$ in islets from control lean mice and ob/ob mice. Right panel shows relative quantification of $Ca_v\beta_3$ protein expression in left panel (n=5, 40 islets in each case). (B,C) Effects of 11 mM glucose on $[Ca^{2+}]_i$ in islets from control and ob/ob mice. Representative traces out of 39 for lean and ob/ob islets are shown. (D) First peak ratios of glucose-induced $[Ca^{2+}]_i$ changes in islets from control lean and ob/ob mice. (E) Oscillation periods of glucose-induced $[Ca^{2+}]_i$ changes in islets from control lean and ob/ob mice. (F) Oscillation amplitudes of glucose-induced $[Ca^{2+}]_i$ changes in islets from control lean mice and ob/ob mice. (G) Effects of 25 mM KCl on $[Ca^{2+}]_i$ in dissociated islet cells from control lean (black) and ob/ob (red) mice. Representative traces in dissociated islet cells from control lean and ob/ob mice are shown. (H) Peak ratios of $[Ca^{2+}]_i$ changes induced by 25 mM KCl in dissociated islet cells from lean (black) and ob/ob (red) mice. (n=10, each experiment included 50 single cells). (I) Glucose-induced insulin release in islets from control lean and ob/ob mice. The islets were treated with 3 mM or 11 mM glucose for 30 min (n=5, 10 islets in each case). (J) Left panel shows intraperitoneal glucose tolerance test in control lean and ob/ob mice (n=5 each). Right panel shows comparison of areas under the curves from left panel. Data are presented as the mean±SEM, *p<0.05, p<0.01, and *p<0.001.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the disclosure can be used in combination, unless the context clearly dictates otherwise.

Voltage-gated $Ca^{2+}$ channels (Cav) are composed of four subunits: a pore-forming α1 subunit, α2/δ, β, and γ subunits. The β subunit is anchored to the intracellular side of the membrane and modifies $Ca^{2+}$ channel currents through binding to the pore-forming α1 subunit. Among the four types of β subunits, the β3 subunit (Cavβ3) is mainly expressed in pancreatic islets in addition to the β2 subunit (Cavβ2). The role of Cavβ3 in diabetes remains unclear.

In a first aspect, the disclosure provides methods for treating or limiting development of diabetes, comprising transplanting into the eye of a subject with diabetes or at risk of diabetes an amount effective to treat or limit development of diabetes of insulin-producing cells engineered to reduce or eliminate expression of a β3 subunit of Cav (Cavβ3). As disclosed in the examples, the inventor has found that the methods and recombinant cells of the disclosure significantly improve the ability to treat or limit development of diabetes compared to transplanted islets engineered to reduce or eliminate expression of a Cavβ3.

In one embodiment, human insulin-producing cells engineered to reduce or eliminate expression of human Cavβ3. As will be understood by those of skill in the art, there are multiple isoforms of human Cavβ3, and the methods may be used to reduce or eliminate expression of any such isoforms, or the genes encoding such isoforms. In various non-limiting embodiments, the human Cavβ3 may comprise the amino acid sequence, or may be encoded by a nucleic acid, as described in NCBI Gene ID entry 784, Ensemble ENSG00000167535 (Gene CACNB3), UniProt database accession P54284, and GenBank mRNA reference sequences NM_000725, NM_001206915, NM_001206916, and NM_001206917; GenPept protein reference sequences NP_000716, NP_001193844, NP_001193845, and NP_001193846.

The cell engineering can comprise any suitable means to reduce expression of Cavβ3, including but not limited to engineering the cells to reduce Cavβ3 gene expression/transcription or protein translation using available genetic engineering techniques. Any suitable reduction in expression will provide a benefit (i.e.: 10%, 15%, 20%, 25%, 30%, 35%, 40%, 45%, 50%, 55%, 60% 65%, 70%, 75%, 80%, 85%, 90%, 95%, or more, or complete elimination in expression.

In a non-limiting embodiment, the methods comprise engineering the cells to reduce expression/transcription of the Cavβ3 gene by any suitable technique, including but not limited to the methods disclosed herein. In one embodiment, each copy of the Cavβ3 gene is disrupted such that gene expression/transcription does not occur, or each copy of the Cavβ3 gene is eliminated.

In various embodiments, the cells are engineered to reduce expression of other proteins, including but not limited to apolipoprotein CIII (apoCIII), one or more chemokines (including but not limited to CCL2, CCL3, CCL5, CXCL1, CXCL9, CXCL10, and/or CXCL11), one or more cytokines (including but not limited to IL-6 and/or IL-8), and/or one or more major histocompatibility complex (MEW) class I proteins (including but not limited to human HLA-A, HLA-B, and/or HLA-C genes). The cell engineering can comprise any suitable means to reduce expression of these other proteins, including but not limited to engineering the cells to reduce gene expression/transcription or protein translation using available genetic engineering techniques. Any suitable reduction in expression will provide a benefit (i.e.: 10%, 15%, 20%, 25%, 30%, 35%, 40%, 45%, 50%, 55%, 60% 65%, 70%, 75%, 80%, 85%, 90%, 95%, or more, or complete elimination in expression.

In a non-limiting embodiment, the methods comprise engineering the cells to reduce expression/transcription of the gene encoding the other proteins by any suitable technique, including but not limited to the methods disclosed herein. In one embodiment, each copy of the protein-encoding gene is disrupted such that gene expression/transcription does not occur, or each copy of the protein encoding gene is eliminated.

In various further embodiments, the cells are engineered to increase expression of other proteins beneficial to insulin producing cell survival and function, including but not limited to GLP1 receptors, insulin receptors, and cytokine IL1B. The cell engineering can comprise any suitable means to increase expression of these other proteins, including but not limited to engineering the cells to increase gene expression/transcription or protein translation using available genetic engineering techniques. Any suitable increase in expression will provide a benefit (i.e.: 10%, 15%, 20%, 25%, 30%, 35%, 40%, 45%, 50%, 55%, 60% 65%, 70%, 75%, 80%, 85%, 90%, 95%, or more.

Any suitable insulin-producing cells may be used. In one embodiment, the insulin-producing cells comprise isolated pancreatic β cells. As used herein, "pancreatic β cells" are any population of cells that contains pancreatic β islet cells. Such pancreatic β islet cell populations include the pancreas, isolated pancreatic islets of Langerhans ("pancreatic islets") and isolated pancreatic β islet cells. As will be understood by those of skill in the art, the beta cells may be transplanted together with other cells (including but not limited to other pancreatic islet cells such as alpha cells, delta cells, epsilon cells, and/or gamma cells; or other cell types of interest), where such other cells may be engineered to, for example, reduce expression of other proteins, including but not limited to one or more chemokines (including but not limited to CCL2, CCL3, CCL5, CXCL1, CXCL9, CXCL10, and/or CXCL11), one or more cytokines (including but not limited to IL-6 and/or IL-8), and/or one or more major histocompatibility complex (MHC) class I proteins (including but not limited to human HLA-A, HLA-B, and/or HLA-C genes).

Transplantation into the eye may involve transplantation into the anterior chamber of the eye. The anterior chamber of the eye comprises the front portion of the eye, and includes the structure in front of the vitreous humour, as well as the cornea, iris, ciliary body, and lens. Transplantation of the cells into the anterior chamber of the eye can comprise placement of the cells into any one or more of these anterior eye chamber compartments. In one non-limiting example, cells are transplanted via injection through the cornea, allowing engraftment of the transplanted cells onto the iris, permitting observation and imaging through the cornea.

Insulin producing cells, such as pancreatic β cells, transplanted in the anterior chamber of the eye engrafted on the iris, become vascularized and innervated, retain their cellular composition, and respond to stimulation. Furthermore, they can be monitored by non-invasive laser scanning microscopy (LSM) allowed in vivo imaging of islet vascularization, innervation as well as beta-cell function and insulin release. In these embodiments, the insulin-producing cells or components thereof can be fluorescently labeled, and fluorescence imaging can be used to monitor cell activity.

Fluorescence imaging on the anterior eye chamber can be accomplished by any technique known to those of skill in the art, including but not limited to laser scanning microscopy. In one embodiment, the methods involve stimulating fluorescence from the labeled cellular components of interest by laser stimulation at appropriate wavelength(s) to non-invasively obtain fluorescence images of the cellular components in the transplanted cells.

In one embodiment, the method is for treating diabetes. In this embodiment, the subject has been diagnosed with type 1 or type 2 diabetes. As used herein, "diabetes" is characterized by insufficient or no production of insulin by the pancreas, leading to high blood sugar levels.

As used herein, "treating diabetes" may mean accomplishing one or more of the following: (a) reducing the severity of the diabetes or diabetic complications; (b) limiting or preventing development of diabetic complications; (c) inhibiting worsening of diabetic complications or of symptoms characteristic of diabetes; (d) limiting or preventing recurrence of diabetic complications or of symptoms characteristic of diabetes; (e) limiting or preventing recurrence of diabetic complications or of symptoms characteristic of diabetes in patients that were previously symptomatic.

Symptoms characteristic of diabetes that can be treated by the methods of the invention include, but are not limited to, elevated blood glucose levels, decreased insulin production, insulin resistance, proteinuria, and impaired glomerular clearance. Diabetic complications that can be treated according to the methods of the invention include, but are not limited to, complications in the nerves (such as diabetic neuropathy) and complications associated with smooth muscle cell dysregulaton (including but not limited to erectile dysfunction, bladder dysfunction, and vascular complications including but not limited to atherosclerosis, stroke, and peripheral vascular disease)

In another embodiment, the method is for limiting development of diabetes. In this aspect, the subject is at risk of type 1 or type 2 diabetes, and a benefit is to limit development of diabetes and/or diabetic complications. Any subject at risk of developing diabetes can be treated, including but not limited to subjects with one or more of, metabolic syndrome, known genetic risk factors for diabetes, a family history of diabetes, and obesity.

In a further embodiment, the methods for treating or limiting development of diabetes and/or diabetic complications may comprise treating those individuals that have been identified as overexpressing Cavβ3 compared to control. Increases in Cavβ3 expression may precede development of diabetic complications, and thus this embodiment permits early detection of suitable patients for treatment using the methods of the invention.

As used herein, "overexpression" is any amount of Cavβ3 expression above control. Any suitable control can be used, including Cavβ3 expression levels from a subject known not to be suffering from diabetes, or previously determined standardized expression levels of Cavβ3 from a population of similar patient samples. Any amount of increased Cavβ3 expression relative to control is considered "overexpression"; in various embodiments, the overexpression comprises at least 10%, 20%, 50%, 100%, 200%, or greater increased Cavβ3 expression compared to control. Cavβ3 can be identified using any suitable technique.

As used herein, the term "subject" or "patient" is meant any subject for which therapy is desired, including humans, cattle, dogs, cats, guinea pigs, rabbits, rats, mice, insects, horses, chickens, and so on. Most preferably, the subject is human.

In another aspect, the disclosure provides engineered cells for carrying out the methods of the disclosure. All embodiments of the engineered cells disclosed for the methods are applicable to the engineered cells of the disclosure In various embodiments, the cells are engineered to reduce expression of other proteins, including but not limited to apolipoprotein CIII (apoCIII), one or more chemokines (including but not limited to CCL2, CCL3, CCL5, CXCL1, CXCL9, CXCL10, and/or CXCL11), one or more cytokines (including but not limited to IL-6 and/or IL-8), and/or one or more major histocompatibility complex (MEW) class I proteins (including but not limited to human HLA-A, HLA-B, and/or HLA-C genes). In various further embodiments, the cells are engineered to increase expression of other proteins beneficial to insulin producing cell survival and function, including but not limited to GLP1 receptors, insulin receptors, and cytokine IL1B. Any suitable insulin-producing cells may be used. In one embodiment, the insulin-producing cells comprise isolated pancreatic β cells, such as human pancreatic β cells.

EXAMPLES

Here, we report that Cavβ3 plays a major role in alterations of $Ca^{2+}$ dynamics and subsequent insulin secretion in the diabetic islets. We observed that the protein level of Cavβ3 in islets from diabetic mice was elevated and that $[Ca^{2+}]i$ dynamics in response to a high glucose concentration were altered. Deficiency of Cavβ3 prevented the alteration of $Ca^{2+}$ signaling during diabetes progression. Decreased expression of Cavβ3 in islets from diabetic mice showed improvement of $[Ca^{2+}]i$ dynamics and insulin secretion compared to islets from control mice, resulting in ameliorated glucose tolerance in the mice. Therefore, targeting of Cavβ3 may be a therapeutic strategy in diabetes, such as T2DM.

RESULTS

Pancreatic Islets from Ob/Ob Mice Overexpress $Ca_v\beta_3$ and have Altered $[Ca^{2+}]_i$ Dynamics and Insulin Secretion We investigated the relationship between diabetes and $Ca_v\beta_3$ using B6.Cg-Lep$^{ob}$/J (ob/ob) mice, a diabetic mouse model. First, we compared $Ca_v\beta_3$ protein levels in islets from 8-12 week-old ob/ob mice with those in islets from lean mice. The protein level of $Ca_v\beta_3$ in islets from ob/ob mice was significantly higher than that in islets from control (lean) mice (FIG. 1A). Considering the phenotype of $Ca_v\beta_3^{-/-}$ mice with the shorter oscillation periods in $Ca^{2+}$ signaling and improved glucose-induced insulin secretion (GIIS), we anticipated opposite changes in ob/ob mice. We measured $[Ca^{2+}]_i$ dynamics in islets from ob/ob and lean mice upon high-glucose (11 mM) stimulation. Representative $Ca^{2+}$ traces are shown in FIG. 1B,C. The first-peak amplitudes in glucose-induced $Ca^{2+}$ traces were lower in islets from ob/ob mice than in those from lean mice (FIG. 1D). For quantitative analysis of the oscillatory patterns, we analyzed the period and amplitude of oscillations based on the power spectral density. Islets from ob/ob mice showed oscillations of longer period and smaller amplitude than islets from lean mice (FIG. 1E,F). To check $Ca^{2+}$ increase dependent on $Ca_v$, we depolarized dissociated islet cells by 25 mM KCl. The $[Ca^{2+}]_i$ peak in islet cells from ob/ob mice was lower than that in islet cells from lean mice (FIG. 1G,H). GIIS was lower in islets from ob/ob mice than in those from lean mice (FIG. 1I). Consistent with these results, glucose intolerance was significantly higher in ob/ob mice than in control lean mice (FIG. 1J). Hence, we observed overexpression of $Ca_v\beta_3$ and alterations in $[Ca^{2+}]_i$ dynamics, including smaller amplitudes of the first peak of glucose induced $Ca^{2+}$ increases and longer oscillation periods/smaller oscillation amplitudes, in islets from ob/ob mice. These changes result in impaired GIIS and overall impaired in vivo glucose tolerance.

Figure 2:
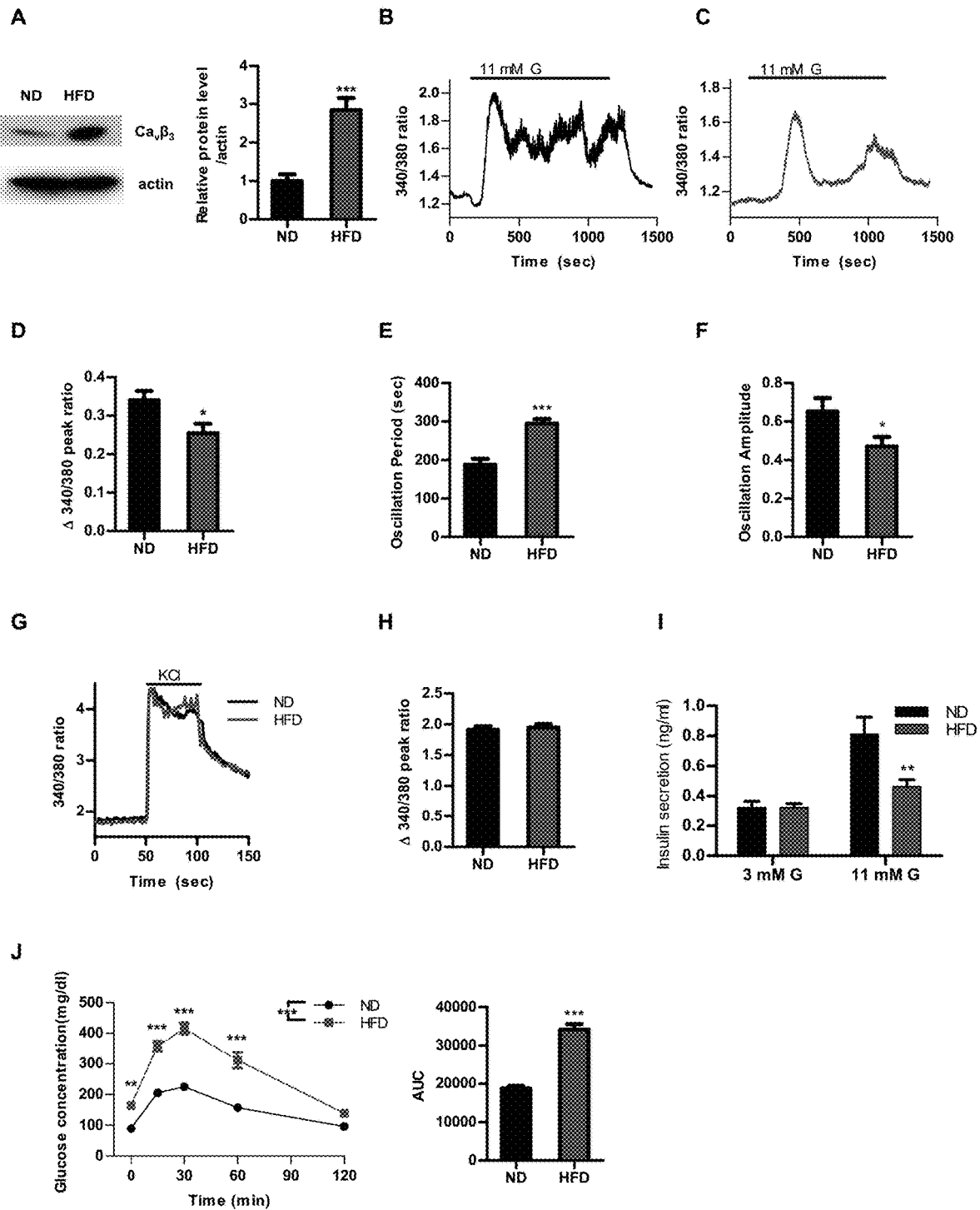
FIG. 2. $Ca_v\beta_3$ expression and $[Ca^{2+}]_i$ dynamics were altered in islets of HFD mice. (A) Left panel shows protein levels of $Cav_v\beta_3$ in islets from NCD and HFD B6 mice. Right panel shows relative quantification of $Ca_v\beta_3$ protein expression in left panel (n=5, 40 islets in each case). (B,C) Effects of 11 mM glucose on $[Ca^{2+}]_i$ in islets from NCD and HFD B6 mice. Representative traces out of 30 for NCD and HFD islets are shown. (D) First peak ratios of glucose-induced $[Ca^{2+}]_i$ changes in islets from NCD and HFD B6 mice. (E) Oscillation periods of glucose-induced $[Ca^{2+}]_i$ changes in islets from NCD and HFD B6 mice. (F) Oscillation amplitudes of glucose-induced $[Ca^{2+}]_i$ changes in islets from NCD and HFD B6 mice. (G) Effects of 25 mM KCl on $[Ca^{2+}]_i$ in dissociated islet cells from NCD (black) and HFD (red) B6 mice. Representative traces on dissociated islet cells from NCD and HFD B6 mice are shown. (H) Peak ratios of $[Ca^{2+}]_i$ changes induced by 25 mM KCl in dissociated islet cells from NCD (black) and HFD (red) B6 mice. (n=10, each experiment involved 50 single cells). (I) Glucose-induced insulin release in islets from NCD and HFD B6 mice. Islets were treated with 3 mM or 11 mM glucose for 30 min (n=5, 10 islets in each case). (J) Left panel shows intraperitoneal glucose tolerance test in NCD and HFD B6 mice (n=5 in each case). Right panel shows comparison of areas under the curves from left panel. Data are presented as the mean±SEM, *p<0.05, p<0.01, and *p<0.001.

Pancreatic Islets from HFD-fed Mice Overexpress $Ca_v\beta_3$ and Show Altered $[Ca^{2+}]_i$ Dynamics and Insulin Secretion Next, we investigated the relationship between $Ca_v\beta_3$ and diabetes using high-fat diet (HFD)-fed mice, another model of T2DM. As in ob/ob mice, the $Ca_v\beta_3$ protein level was higher in islets from mice fed a HFD for 8 weeks than in islets from normal chow diet (NCD)-fed mice (FIG. 2A). Representative $Ca^{2+}$ traces upon 11 mM glucose stimulation are shown in FIG. 2B,C. First-peak amplitudes in glucose-induced $Ca^{2+}$ traces were lower in islets from HFD-fed mice compared to those of NCD-fed mice (FIG. 2D). Based on the power spectral density, we found that islets from HFD-fed mice produced oscillations of longer period (FIG. 2E) and smaller amplitude (FIG. 2F). However, 25 mM KCl did not induce significant differences in $Ca^{2+}$ influx between islets from HFD-fed mice and those from NCD-fed mice (FIG. 2G,H). Nevertheless, GIIS was lower in islets from HFD-fed mice than in islets from NCD-fed mice (FIG. 2I). HFD-fed mice showed stronger glucose intolerance than NCD-fed mice (FIG. 2J). Collectively, these results revealed overexpression of $Ca_v\beta_3$, alterations in $Ca^{2+}$ dynamics and insulin secretion in islets from HFD-fed mice, similar to the observations made in ob/ob mice. Based on these findings, which were opposite to the results obtained in $Ca_v\beta_3^{-/-}$ mice, we suspected that overexpression of $Ca_v\beta_3$ might be causative factor underlying altered $[Ca^{2+}]_i$ dynamics and insulin secretion in diabetic islets.

Figure 3:
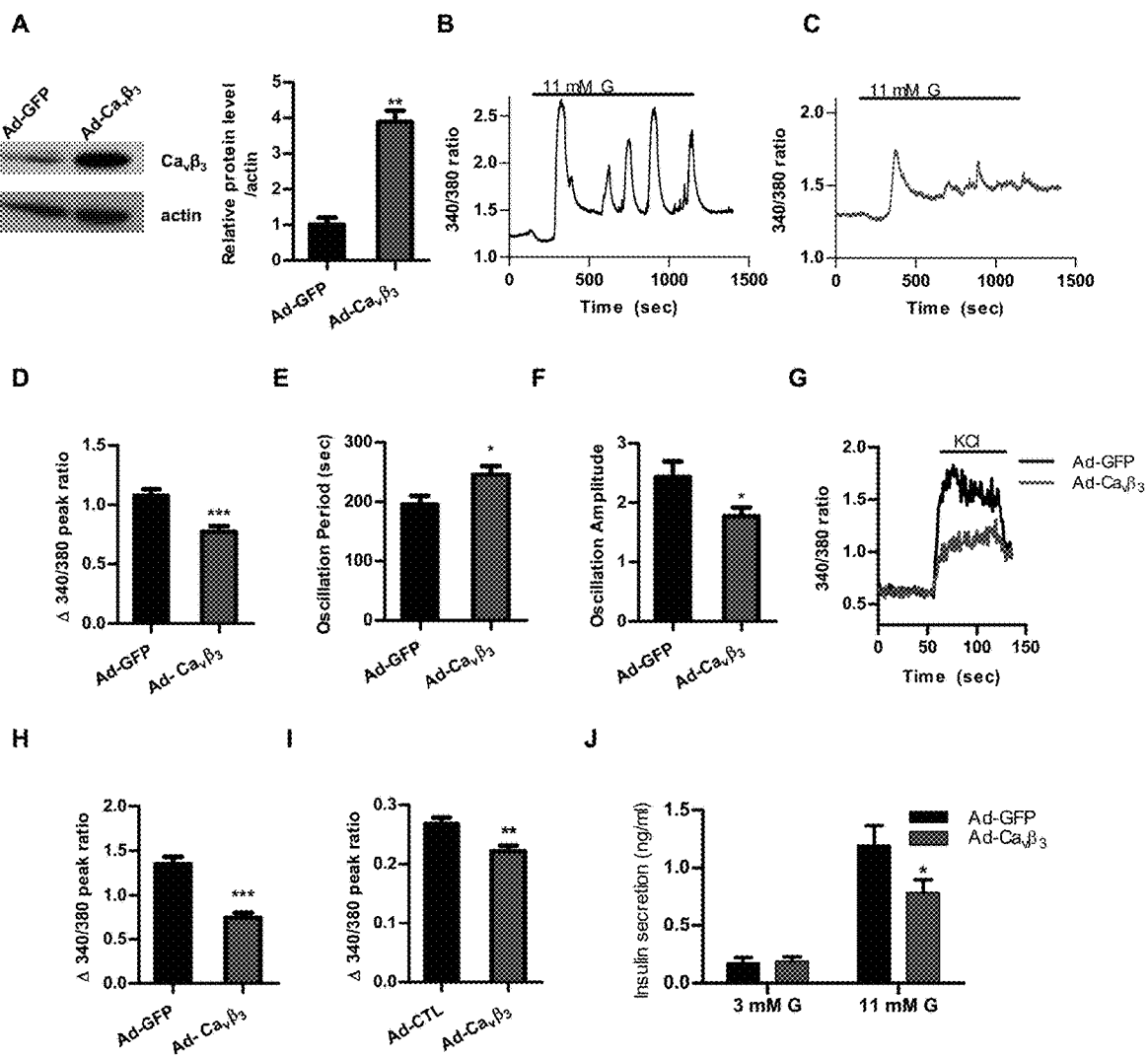
FIG. 3. Overexpression of $Ca_v\beta_3$ altered $[Ca^{2+}]_i$ dynamics in pancreatic islets. (A) Left panel shows protein levels of $Ca_v\beta_3$ in control and $Ca_v\beta_3$-overexpressing adenovirus treated islet. Right panel shows relative quantification of $Ca_v\beta_3$ protein levels in left panel (n=5, 40 islets in each case). (B,C) Effects of 11 mM glucose on $[Ca^{2+}]_i$ in control and $Ca_v\beta_3$-overexpressing islets. Representative traces out of 30 for both control and $Ca_v\beta_3$-overexpressing islets are shown. (D) First peak ratios of glucose-induced $[Ca^{2+}]_i$ changes in control and $Ca_v\beta_3$-overexpressing islets. (E) Oscillation periods of glucose-induced $[Ca^{2+}]_i$ changes in control and $Ca_v\beta_3$-overexpressing islets. (F) Oscillation amplitudes of glucose-induced $[Ca^{2+}]_i$ changes in control and $Ca_v\beta_3$-overexpressing islets. (G) Effects of 25 mM KCl on $[Ca^{2+}]_i$ in control islet cells (black) and $Ca_v\beta_3$-overexpressing islet cells (red). Representative traces of each group are shown. (H) Peak ratios of $[Ca^{2+}]_i$ changes induced by 25 mM KCl in control islet cells (black) and $Ca_v\beta_3$-overexpressing islet cells (red) (n=10, each experiment involved 50 single cells). (I) Peak ratios of $[Ca^{2+}]_i$ changes induced by 200 uM Cch in control islet cells and $Ca_v\beta_3$-overexpressing islet cells (n=5, each experiment involved 30 single cells). (J) Glucose-induced insulin release in control and $Ca_v\beta_3$-overexpressing islets. Islets were treated with 3 mM or 11 mM glucose for 30 min (11 mM glucose/3 mM glucose) are shown (n=5, 10 islets in each case). The data are presented as the mean±SEM, *p<0.05, p<0.01, and *p<0.001.

$Ca_v\beta_3$ Overexpression in Pancreatic Islets Alters $[Ca^{2+}]_i$ Dynamics and Insulin Secretion To investigate whether the altered $[Ca^{2+}]_i$ dynamics and impaired insulin secretion in diabetic islets are directly resulting from $Ca_v\beta_3$ overexpression, we measured these parameters in islets from C57BL/6 mice overexpressing $Ca_v\beta_3$ (FIG. 3A) and compared with islets from control mice. First-peak amplitudes in the glucose-induced $Ca^{2+}$ traces were lower in islets overexpressing $Ca_v\beta_3$ than in control islets expressing green fluorescent protein (FIG. 3B-D). Oscillation periods were longer and amplitudes smaller in islets from $Ca_v\beta_3$-overexpressing mice compared to those from control mice (FIG. 3E,F). Upon depolarization of dissociated islet cells with 25 mM KCl, $[Ca^{2+}]_i$ peak amplitudes in islet cells overexpressing $Ca_v\beta_3$ were lower than those in control islet cells (FIG. 3G,H). In our previous study, we suggested that an increase in $IP_3$-mediated $Ca^{2+}$ release from ER might contribute to changes in $[Ca^{2+}]_i$ oscillation frequency and insulin secretion in $Ca_v\beta_3$ KO islets (Berggren et al., 2004). To check whether this mechanism is involved in islets overexpressing $Ca_v\beta_3$, we stimulated islet cells overexpressing $Ca_v\beta_3$ and control islet cells with Carbamylcohline (Cch), triggering the cholinergic/$IP_3$ signalling pathway. The resulting peak in $[Ca^{2+}]_i$ increase in islet cells overexpressing $Ca_v\beta_3$ were lower than that in controls (FIG. 3I). GIIS was also lower after stimulation with 11 mM glucose in islet cells overexpressing $Ca_v\beta_3$ (FIG. 3J). The results obtained in islets or islet cells overexpressing $Ca_v\beta_3$ were consistent with the findings in ob/ob and HFD-fed mice. To shed some light on how $Ca_v\beta_3$ levels can be elevated in diabetic islets, we investigated potential effects of several factors, such as glucose, insulin, and inflammatory cytokines, known to be associated with diabetes progression. TNF-α or IL-1β significantly increased protein levels of $Ca_v\beta_3$ in isolated islets (data not shown). This suggests that proinflammatory cytokines may induce overexpression of $Ca_v\beta_3$ in islets and thereby cause islet cell dysfunction.

Figure 4:
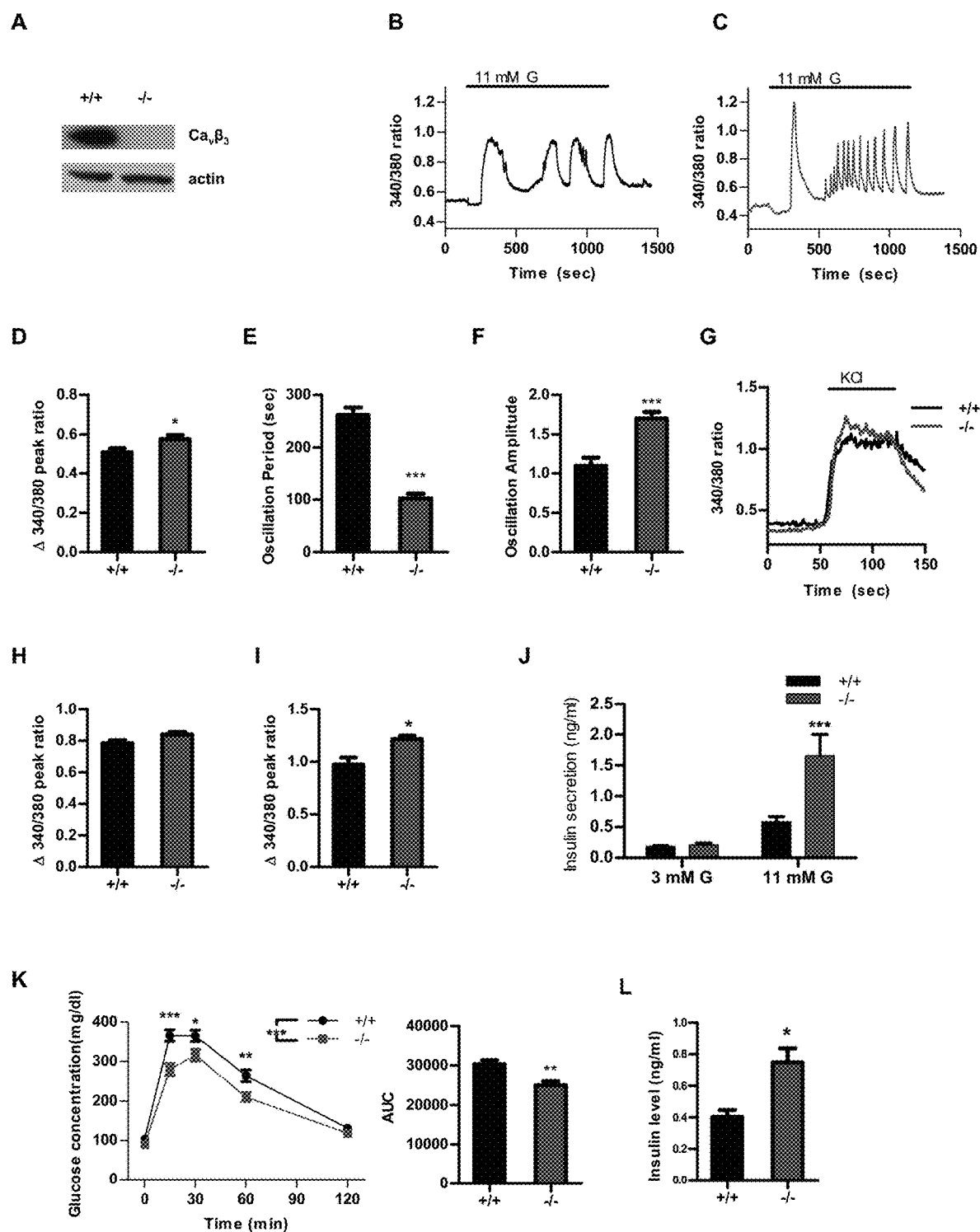
FIG. 4. $Ca_v\beta_3^{-/-}$ mice feed a HFD show a less severe diabetic phenotype. (A) Protein levels of $Ca_v\beta_3$ in islets from control mice fed a HFD and $Ca_v\beta_3^{-/-}$ mice fed a HFD (n=5, 40 islets in each case). (B,C) Effects of 11 mM glucose on $[Ca^{2+}]_i$ in islets from control mice fed a HFD and $Ca_v\beta_3^{-/-}$ mice fed a HFD. Representative traces out of 30 are shown. (D) First peak ratios of glucose-induced $[Ca^{2+}]_i$ changes in islets from control mice and $Ca_v\beta_3^{-/-}$ mice fed a HFD. (E) Oscillation periods of glucose-induced $[Ca^{2+}]_i$ changes in islets from control mice and $Ca_v\beta_3^{-/-}$ mice fed a HFD. (F) Oscillation amplitudes of glucose-induced $[Ca^{2+}]_i$ changes in islets from control mice and $Ca_v\beta_3^{-/-}$ mice fed a HFD. (G) Effects of 25 mM KCl on $[Ca^{2+}]_i$ in dissociated islet cells from control mice (black) and $Ca_v\beta_3^{-/-}$ mice (red) fed a HFD. Representative traces on dissociated islet cells are shown. (H) Peak ratios of $[Ca^{2+}]_i$ changes induced by 25 mM KCl in dissociated islet cells from control mice (black) and $Ca_v\beta_3^{-/-}$ mice (red) fed a HFD (n=5, each experiment involved 50 single cells). (I) Peak ratios of $[Ca^{2+}]_i$ changes induced by 200 uM Cch in dissociated islet cells from $Ca_v\beta_3^{-/-}$ mice feed a HFD and control mice feed a HFD (n=5, each experiment involved 30 single cells). (J) Glucose-induced insulin release from islets of control and $Ca_v\beta_3^{-/-}$ mice fed a HFD. Islets were treated with 3 mM or 11 mM glucose for 30 min (n=3, 10 islets in each case). (K) Left panel shows intraperitoneal glucose tolerance test of control and $Ca_v\beta_3^{-/-}$ mice fed a HFD (n=4 in each case). Right panel shows comparison of areas under the curves from left panel. (L) Plasma insulin levels 30 min after glucose injection from fasted control mice (black) and $Ca_v\beta_3^{-/-}$ mice (red) fed a HFD (n=5 in each case). Data are presented as the mean±SEM, *p<0.05, p<0.01, and *p<0.001.

Pancreatic Islets from $Ca_v\beta_3^{-/-}$ Mice Exposed to HFD have Ameliorated $[Ca^{2+}]_i$ Dynamics and Insulin Secretion We examined whether $Ca_v\beta_3$ had a direct role in the islet dysfunction observed in the HFD model. $Ca_v\beta_3^{-/-}$ mice and their littermate controls were fed HFD for eight weeks, and no significant difference in body weight changes was observed between the two groups (data not shown). Next, we investigated $[Ca^{2+}]_i$ dynamics in the islets from control and $Ca_v\beta_3^{-/-}$ mice (FIG. 4B,C). First-peak amplitudes in the glucose-induced $Ca^{2+}$ traces were higher in islets from HFD-fed $Ca_v\beta_3^{-/-}$ mice than in those from control animals fed the HFD (FIG. 4D). $Ca_v\beta_3^{-/-}$ islets showed shorter oscillation periods and larger amplitudes (FIG. 4E,F). There was no significant difference in the $[Ca^{2+}]_i$ peak after stimulation with 25 mM KCl between $Ca_v\beta_3^{-/-}$ and control islet cells (FIG. 4G,H). This was in agreement with similar KCl-stimulated responses in islets from control mice fed NCD and in islets from control mice fed HFD (FIG. 2H). We also compared effects of Cch on in islets from $Ca_v\beta_3^{-/-}$ mice and their littermate controls fed HFD. $Ca_v\beta_3^{-/-}$ islets showed increased peak of $[Ca^{2+}]_i$ compared to control islets (FIG. 4I), which is consistent with the Cch effect in islets overexpressing $Ca_v\beta_3$ (FIG. 3I). The compromised GIIS in islets from HFD-fed mice was also improved in islets from HFD-fed $Ca_v\beta_3^{-/-}$ mice (FIG. 4J). Consistent with the results on $[Ca^{2+}]_i$ dynamics and insulin secretion, glucose tolerance in $Ca_v\beta_3^{-/-}$ mice on HFD was better than that in control mice (FIG. 4K), while insulin tolerance was not significantly different (data not shown). Plasma insulin level at 30 min after glucose injection was higher in HFD-fed $Ca_v\beta_3^{-/-}$ mice (FIG. 4L). Although the fasting insulin level was not significantly different in HFD-fed $Ca_v\beta_3^{-/-}$ mice compared to lean mice (data not shown), non-fasting insulin levels was higher in HFD-fed $Ca_v\beta_3^{-/-}$ mice (data not shown). Therefore it is likely that an increase in in vivo GIIS explains the better glucose tolerance in HFD-fed $Ca_v\beta_3^{-/-}$ mice. Based on these observations, we suggest that overexpression of $Ca_v\beta_3$ is an important factor causing islet dysfunction in diabetes development, and regulation of the $Ca_v\beta_3$ level could lead to an improvement of islet function and glucose homeostasis.

Figure 5:
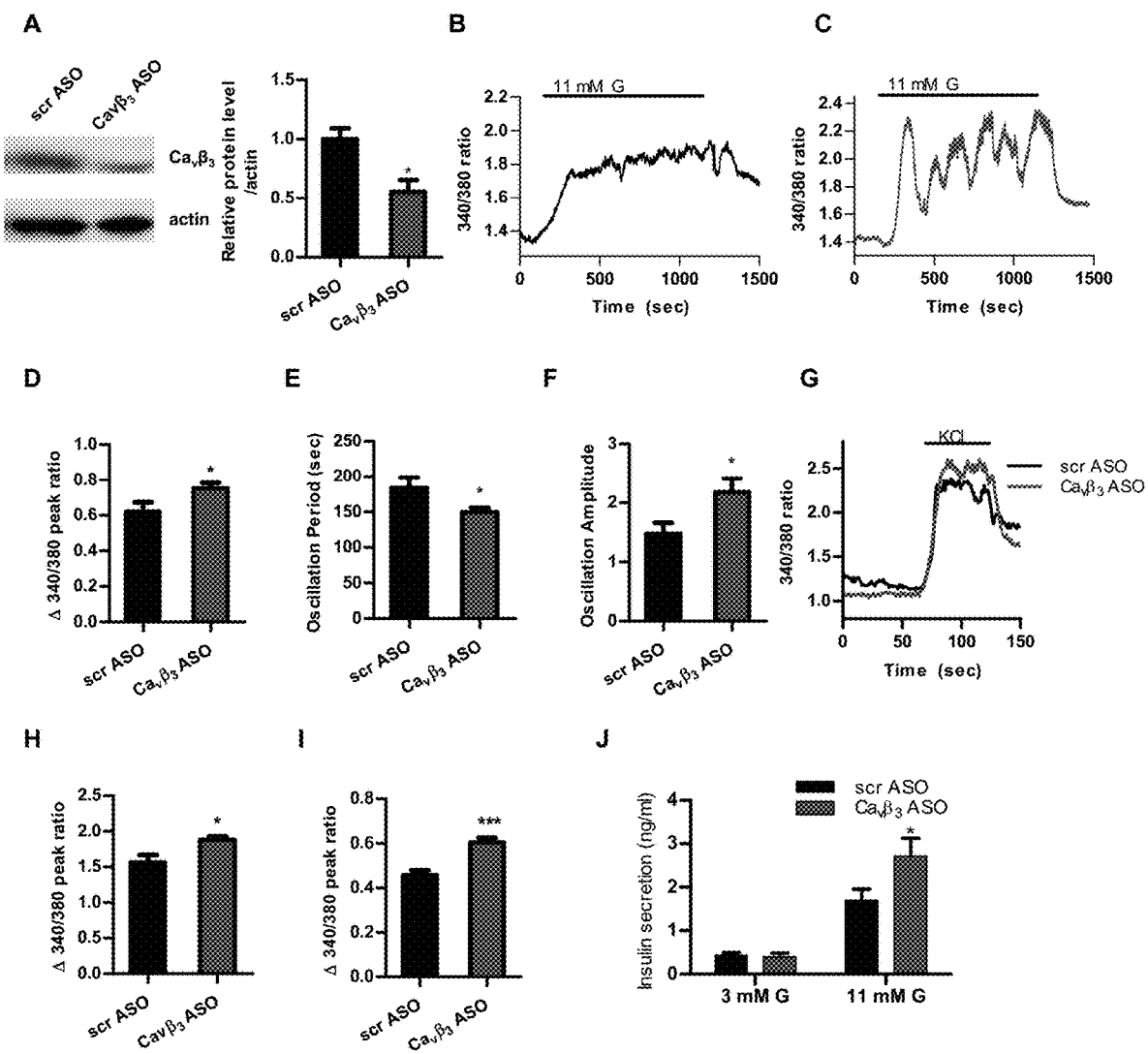
FIG. 5. Treatment with antisense-oligonucleotide targeting $Ca_v\beta_3$ improves $[Ca^{2+}]_i$ dynamics and insulin secretion in ob/ob islets. (A) Left panel shows protein levels of $Ca_v\beta_3$ in ob/ob islets treated with scramble ASO and $Ca_v\beta_3$ ASO. Right panel shows relative quantification of $Ca_v\beta_3$ protein levels in (left) (n=5, 40 islets in each case). (B,C) Effects of 11 mM glucose on $[Ca^{2+}]_i$ in ob/ob islets treated with scramble ASO and $Ca_v\beta_3$ ASO. Representative traces out of 30 are shown. (D) First peak ratios of glucose-induced $[Ca^{2+}]_i$ changes in ob/ob islets treated with scramble ASO and $Ca_v\beta_3$ ASO. (E) Oscillation periods of glucose-induced $[Ca^{2+}]_i$ changes in ob/ob islets treated with scramble ASO and $Ca_v\beta_3$ ASO. (F) Oscillation amplitudes of glucose-induced $[Ca^{2+}]_i$ changes in ob/ob islets treated with scramble ASO and $Ca_v\beta_3$ ASO. (G) Effects of 25 mM KCl on $[Ca^{2+}]_i$ in dissociated islet cells from scramble ASO (black) and $Ca_v\beta_3$ ASO treated (red) ob/ob mice. Representative traces on dissociated islet cells are shown. (H) Peak ratios of $[Ca^{2+}]_i$ changes induced by 25 mM KCl in dissociated islet cells from scramble ASO (black) and $Ca_v\beta_3$ ASO treated (red) ob/ob mice (n=5, each experiment involved 50 single cells). (I) Peak ratios of $[Ca^{2+}]_i$ changes induced by 200 uM Cch in ob/ob dissociated islet cells treated with scramble ASO and $Ca_v\beta_3$ ASO (n=5, each experiment involved 30 single cells). (J) Glucose-induced insulin release in ob/ob islets treated with scramble ASO and $Ca_v\beta_3$ ASO. The islets were treated with 3 mM or 11 mM glucose for 30 min (n=5, 10 islets in each case). Data are presented as the means±SEM, *p<0.05.

Treatment with Antisense-Oligonucleotide Targeting $Ca_v\beta_3$ Improves $[Ca^{2+}]_i$ Dynamics and Insulin Secretion in Ob/Ob Islets Next question was whether decreasing expression of $Ca_v\beta_3$ could improve $Ca^{2+}$ dynamics and insulin secretion in the diabetes onset condition. We tested this idea in ob/ob islets from 8-12 week-old mice by treatment with antisense-oligonucleotide targeting $Ca_v\beta_3$ ($Ca_v\beta_3$ ASO). Treatment with $Ca_v\beta_3$ ASO effectively reduced $Ca_v\beta_3$ expression in the ob/ob islets (FIG. 5A). We measured glucose-induced $Ca^{2+}$ dynamics in ob/ob islets treated with $Ca_v\beta_3$ ASO or scramble ASO (FIG. 5B,C). First-peak amplitudes in glucose-induced $Ca^{2+}$ traces were significantly higher in ob/ob islets after $Ca_v\beta_3$ ASO treatment (FIG. 5D). Islets treated with $Ca_v\beta_3$ ASO showed shorter oscillation periods (FIG. 5E) and larger amplitudes (FIG. 5F), as indicated by power spectral analysis. Upon stimulation with 25 mM KCl, dissociated islet cells treated with $Ca_v\beta_3$ ASO showed higher $Ca^{2+}$ peak ratios than islet cells treated with scramble ASO (FIG. 5G,H). Moreover, treatment with $Ca_v\beta_3$ ASO, compared to treatment with scramble ASO, increased Cch-induced $Ca^{2+}$ release in islet cells from ob/ob mice (FIG. 5I). Consistent with the $Ca^{2+}$-influx results, islets treated with $Ca_v\beta_3$ ASO showed improved GIIS (FIG. 5J).

Figure 6:
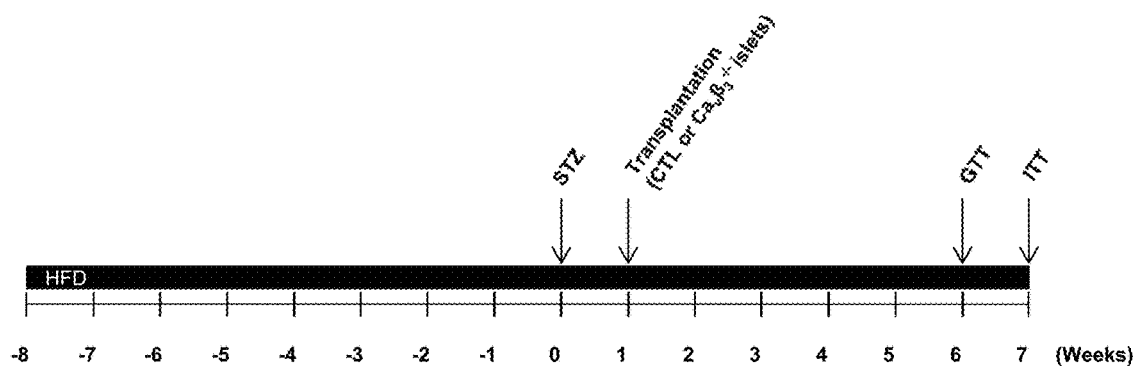
FIG. 6. Metabolic transplantation of $Ca_v\beta_3^{-/-}$ islet improves glucose control under diabetic conditions. (A) Schematic diagram of experimental protocol. (B) Representative photograph of islets engrafted on the iris. (C) Representative islet vessel images, maximum projections of image stacks of an islet graft in the anterior chamber of the eye three weeks after transplantation. Islet is green and blood vessels are red (Texas Red staining). Scale bar=100 um. (D) Left panel shows intraperitoneal glucose tolerance tests in HFD fed mice transplanted with islets from control and $Ca_v\beta_3^{-/-}$ mice (n=8 in each case). Right panel shows Comparison of areas under the curves from left panel. (E) Intraperitoneal insulin tolerance test in HFD fed mice transplanted with islets from control and $Ca_v\beta_3^{-/-}$ mice (n=8 in each case). Data are presented as the mean±SEM, *p<0.05 and **p<0.01.
Figure 6:
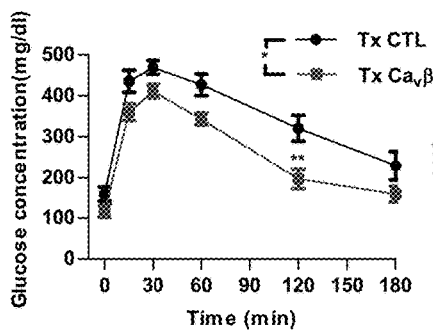
Figure 6:
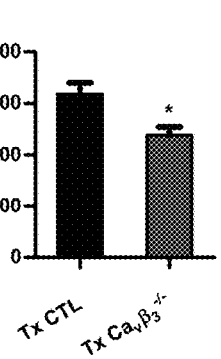
Figure 6:
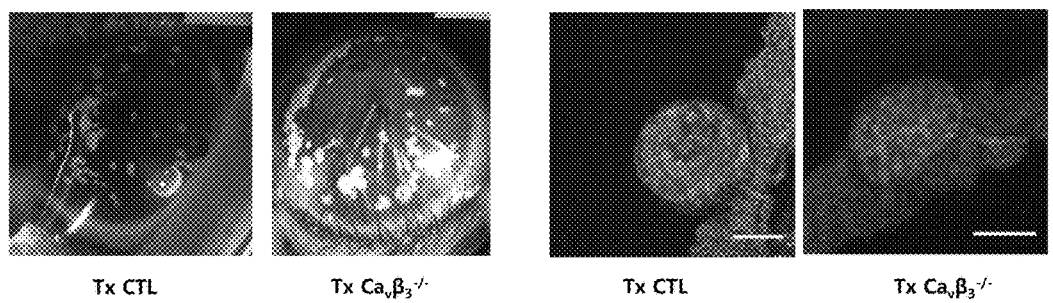
Figure 6:
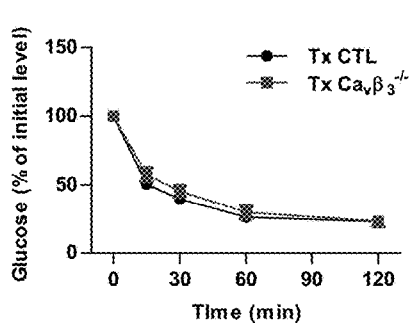

Transplantation of $Ca_v\beta_3^{-/-}$ Islets Improves Glycemic Control in HFD-Fed Mice To assess the effect of targeting $Ca_v\beta_3$ in pancreatic islets after diabetes onset in vivo, we transplanted islets from $Ca_v\beta_3^{-/-}$ mice and control littermates into the anterior chamber of the eye in diabetic mice. C57BL/6J mice were put on a HFD during the whole period of the experiment. After eight weeks of HFD feeding, the animals were treated with streptozotocin to avoid an effect of endogenous pancreatic islets. Thereafter islet transplantations were performed (FIG. 6A,B). Three weeks later, we imaged islet vascularization in vivo (FIG. 6C). Vessel diameters inside the islets did not significantly differ between $Ca_v\beta_3^{-/-}$ islet-transplanted and control islet-transplanted mice (data not shown). The blood glucose level was decreased in both $Ca_v\beta_3^{-/-}$ and control islet-transplanted mice (data not shown). After 4 weeks, when transplanted islets are fully vascularized and innervated, we performed glucose tolerance tests. From five weeks after transplantation, glucose tolerance in mice transplanted with $Ca_v\beta_3^{-/-}$ islets improved as compared with mice transplanted with control islets. We presented the results obtained six weeks after transplantation, when glucose tolerance was more significantly improved. The area under the curve was significantly lower in $Ca_v\beta_3^{-/-}$ islet-transplanted compared to control islet-transplanted mice (FIG. 6D). However, insulin tolerance was not significantly different (FIG. 6E). In short, glucose clearance, but not insulin sensitivity, was improved in $Ca_v\beta_3^{-/-}$ islet-transplanted mice. These results suggest that suppression of $Ca_v\beta_3$ after the time of onset of diabetes can significantly improve the diabetes phenotype in mice.

Overexpression of $Ca_v\beta_3$ Disrupts GIIS in Human Islets

Figure 7:
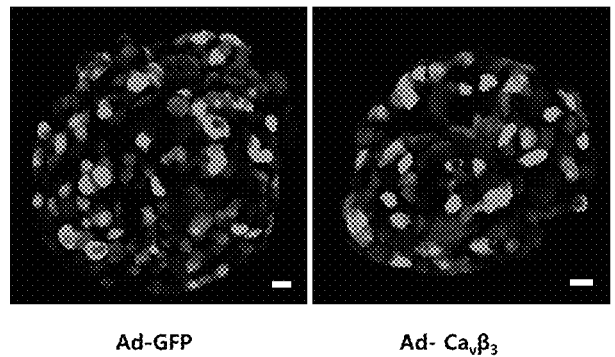
FIG. 7. Ad-$Ca_v\beta_3$ transduced human islets display impaired glucose-stimulated insulin secretion. (A) Sample confocal images of control (left panel) and $Ca_v\beta_3$-overexpressing human islets (right panel). (B) Insulin secretion from control or $Ca_v\beta_3$-overexpressing islets of individual human donors incubated with 3 mM or 11 mM glucose. (C) Average insulin secretion from control or $Ca_v\beta_3$-overexpressing islets of human donors incubated with 3 mM or 11 mM glucose. Data are presented as mean±SEM. #P<0.01 vs. 3 mM glucose/Ad-GFP, and °P<0.05 vs 11 mM glucose/Ad-GFP and **P<0.01 vs. 11-3 mM glucose/Ad-GFP. Scale bars=20 μm. Δ Insulin: insulin released from islets incubated with 11 mM glucose minus that from islets incubated with 3 mM glucose.
Figure 7:
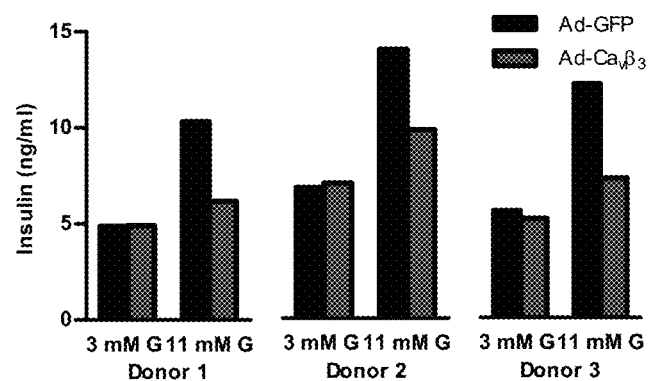
Figure 7:
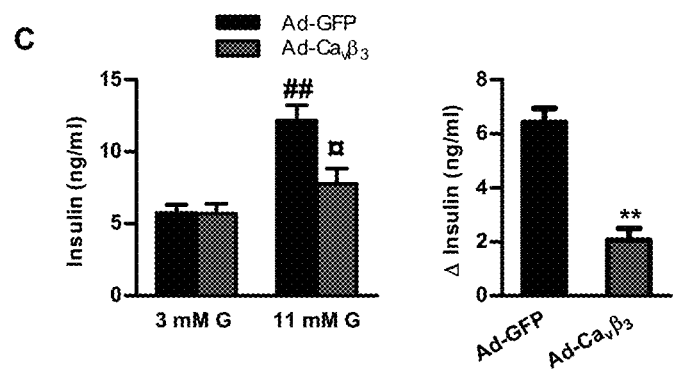

To investigate whether $Ca_v\beta_3$ functions in human islets, we overexpressed $Ca_v\beta_3$ in islets from individual donors using adenovirus (FIG. 7A) and measured GIIS. Overexpression of $Ca_v\beta_3$ decreased insulin secretion specifically in the presence of a high glucose concentration, whereas it didn't affect basal insulin secretion (FIG. 7B,C). From these results we suggest that overexpression of $Ca_v\beta_3$ might have a similar role in human islets as in rodent islets, namely decreasing GIIS.

DISCUSSION

In this study, we showed that $Ca_v\beta_3$ was overexpressed in diabetic mouse islets and that this was important for progression of T2DM. Based on our results obtained with ASO treatment and islet transplantation, we suggest that $Ca_v\beta_3$ could be a target for treatment of T2DM.

Overexpression of $Ca_v\beta_3$ in pancreatic islets led to alterations in $Ca^{2+}$ dynamics during diabetes progression. In our experiments using islets from ob/ob and HFD-fed mice, we also consistently observed that these phenotypes concur with overexpression of $Ca_v\beta_3$, and that overexpression of $Ca_v\beta_3$ per se induced similar changes in $Ca^{2+}$ dynamics. In a series of experiments where we reduced $Ca_v\beta_3$ expression in diabetic islets, the changes in $Ca^{2+}$ dynamics were reversed. Together, these results indicate that $Ca_v\beta_3$ is responsible for the alterations in $Ca^{2+}$ dynamics in diabetic mouse islets.

We propose $Ca_v\beta_3$ as a potential target for diabetes treatment. We showed that decreasing the level of $Ca_v\beta_3$ in ob/ob islets recovered their GIIS, and that transplantation of $Ca_v\beta_3^{-/-}$ islets into HFD-induced diabetic mice could recover glucose intolerance. Insulin secretion assays showed that manipulation of $Ca_v\beta_3$ affected secretion only at elevated glucose concentrations (FIG. 4L). This means that targeting $Ca_v\beta_3$ is not associated with risk for hypoglycemia, one of the main issues associated with the strategy of augmenting insulin secretion in patients with T2DM. Our data demonstrating that overexpression of $Ca_v\beta_3$ decreased GIIS also in human islets (FIG. 7), supports the notion that $Ca_v\beta_3$ may indeed represent a promising clinical target in the treatment of diabetes. To develop treatment strategies for diabetes targeting $Ca_v\beta_3$, two approaches can be considered. One is to decrease the level of $Ca_v\beta_3$ in pancreatic islets by ASO or siRNA treatment, alternatively to transplant islets in which the endogenous expression levels of $Ca_v\beta_3$ have been suppressed. The other is to block $Ca_v\beta_3$ function.

METHOD DETAILS

Experimental Animal Care and Islet/Cell Preparation

All experimental procedures were approved by the Pohang University of Science and Technology Institutional Animal Care and Use Committee (POSTECH-2015-0055-R1, POSTECH IACUC, Korea). C57BL/6J, B6.Cg-Lep$^{ob}$/J male mice (Jackson Laboratory, Bar Harbor, Me., USA) were used. $Ca_v\beta_3^{-/-}$ mice were generated and backcrossed over 18 generation. $Ca_v\beta_3$ heterozygous ($Cav\beta_3^{+/-}$) mice were backcrossed into C57BL/6J. Wild-type ($Ca_v\beta_3^{+/+}$) and $Ca_v\beta_3^{-/-}$ mice used for analyses were obtained by breeding $Cav\beta_3^{+/-}$ mice. The animals were maintained with a 12-h light/dark cycle with free access to water. Mice were sacrificed by cervical dislocation under anesthesia with $CO_2$. Four-week-old mice were fed a 60% HFD (D12492, Research Diets, Inc., New Brunswick, N.J., USA) for 8 weeks and body weight and food intake were monitored. Islets of Langerhans were isolated by collagenase digestion (1 mg/ml collagenase P; Roche Diagnostics, Indianapolis, Ind.) and subsequently handpicked under a stereomicroscope. Islets were cultured in RPMI 1640 medium (Gibco, Carlsbad, Calif.) supplemented with 10% FBS, 100 U/ml penicillin, and 100 µg/ml streptomycin at 37° C. in a humidified atmosphere of 5% $CO_2$ in air for one day before the experiment. Single islet cells were obtained by shaking islets in $Ca^{2+}$-free medium with Accutase™ (Gibco) and seeded on poly-L-lysine-coated glasses and cultured overnight in RPMI 1640 culture medium. For treatment with proinflammatory cytokines, islets were pooled and incubated at 20 ng/ml TNF-α (R&D Systems, Minneapolis, Minn.) or 20 ng/ml IL-1β (R&D Systems) in RPMI 1640 medium (Gibco) supplemented with 10% FBS, 100 U/ml penicillin, and 100 µg/ml streptomycin at 37° C. in a humidified atmosphere of 5% $CO_2$ for 24 hr.

$[Ca^{2+}]_i$ Measurements $[Ca^{2+}]_i$ was measured using the Fura2-AM method. Islets or islet cells were incubated with Fura2™-AM (2 µmol/l, Invitrogen, Carlsbad, Calif.) in HEPES buffer (125 mM NaCl, 5.9 mM KCl, 2.56 mM $CaCl_2$, 1.2 mM $MgCl_2$, 25 mM HEPES, 3 mM glucose, 0.1% BSA, pH 7.4) for 30 min at 37° C. under 5% $CO_2$. After loading, glass coverslips containing islets and cells were mounted into an open perifusion chamber and maintained at 37° C., and $[Ca^{2+}]_i$ was measured as the 340/380 nm fluorescence ratio. Islets were stimulated with 11 mM glucose, 25 mM KCl or 200 uM Cch (Sigma-Aldrich). The light source was equipped with a xenon arc lamp and an integrated shutter (Lambda DG-4; Sutter Instrument Company, Novato, Calif.), and coupled to the microscope (IX 71; Olympus, Tokyo, Japan) via a liquid light guide. Sixteen-bit gray-scale images with a binning of 1×1 were captured every second (exposure time ~100 ms) with a cooled EM-CCD camera (ImagEM™ X2; Hamamatsu Photonics, Hamamatsu, Japan). The camera and shutter were controlled by MetaFluor™ software (MDS Analytical Technologies, Sunnyvale, Calif.). Data were analyzed with the same software. Cells with bright $[Ca^{2+}]_i$ signal defined the regions of interest (ROIs). ROI signals were calculated by subtracting background noise signal. $[Ca^{2+}]_i$ oscillations were analyzed using power spectral analysis in Matlab™ (MathWorks, Lowell, Mass.) with a code adapted for analysis of the oscillations in pancreatic islets (Uhlen, 2004) with modification. Oscillation amplitude values were calculated as the square root of the total power of periods from 6 to 600 s. The fast Fourier transform power spectrum was used to determine the dominating oscillation period from respective power spectra.

SDS-PAGE and Immunoblot Analysis

Islets were lysed in Laemmli sample buffer and heated at 95° C. for 5 min. Proteins were separated in SDS-page gels (6-16% gradient) and transferred to nitrocellulose membranes (Whatman, Maidstone, UK). Blots were blocked for 30 min with 5% skim milk, incubated with $Ca_v\beta_3$ antibody (1:2000, C1978, Sigma-Aldrich), BIP (1:1000, 3177, Cell Signaling Technology, Danvers, Mass.), ATF-6α (1:100, sc-166659, Santa Cruz Biotechnology. Inc., Santa Cruz, Calif.) or␣ARE1α (1:1000, 3294, Cell Signaling Technology) at 4° C. overnight, and washed 3 times with washing buffer (50 mM Tris aminomethane, 150 mM NaCl, and 0.05% Tween). The membranes were incubated with secondary antibody (rabbit) at room temperature for 1 h and washed 3 times with washing buffer. Immunoreactive bands were visualized with the ECL Plus immunoblotting detection system (Thermo Scientific, Waltham, Mass.).

Recombinant Adenovirus and Antisense-Oligonucleotides

Adenovirus overexpressing $Ca_v\beta_3$ construct was generated through homologous recombination between linearized pAd-Track™-CMV vector carrying either Flag2-WT or Flag2-$Ca_v\beta_3$ and the adenoviral backbone vector pAd-Easy™. Ad-green fluorescent protein was used as a control for all experiments. Viruses were purified with an Adeno-X Maxi purification kit (Clontech, Palo Alto, Calif., USA) and titrated according to the manufacturer's instructions. Antisense-oligonucleotides, a series of chimeric 20-mer phosphorothioate oligonucleotides containing 2'-O-methoxyethyl groups at positions 1-5 and 16-20 targeted to mouse $Ca_v\beta_3$, were synthesized and purified (IDT, Coralville, IOWA, USA). Adenovirus and antisense-oligonucleotides were added directly to pancreatic islet in the culture medium, 4 h and overnight, respectively.

Glucose and Insulin Tolerance Tests

For glucose tolerance tests, mice were fasted overnight and 1 g/kg of D-glucose (Sigma-Aldrich) was injected intraperitoneally. For insulin tolerance tests, mice were fasted for 4 h and 0.2 U/kg of insulin (Eli Lilly & Co., Indianapolis, Ind., USA) was injected intraperitoneally. Blood samples were collected at 0, 15, 30, 60, and 120 min after injection by tail bleeding. Blood glucose levels were determined using a glucometer (Accu-Check™ Active, Roche Diagnostics).

Insulin Release

Ten islets isolated from corresponding mice were pooled and incubated at 3 mM or 11 mM glucose in HEPES buffer for 30 min at 37° C. The conditioned buffer was collected, and insulin concentration was measured with the Rat/Mouse Insulin ELISA kit (ALPCO Diagnostics, Salem, N.H.), according to manufacturer's instruction. GSIS data are normalized by the number of islets. For experiments with human islets, groups of 10 human islets infected with Ad-GFP or Ad-$Ca_v\beta_3$ were preincubated with 3 mM glucose in Krebs buffer at 37° C. for 1 h. Subsequently, preincubated islets were treated with 3 mM glucose and then 11 mM glucose in Krebs buffer at 37° C. for 1 h. Samples were collected for insulin secretion assay. Insulin concentrations in the collected samples were determined by using AlphaLISA™ assay. Krebs buffer consisted of (in mM) 119 NaCl, 20 HEPES, 4.6 KCl, 2 $CaCl_2$, 1 $MgSO_4$, 0.15 $Na_2HPO_4$, 0.4 $KH_2PO_4$, 5 $NaHCO_3$ and 0.1% BSA (pH 7.4). Human pancreata were obtained within the Nordic Network for Islet Transplantation from deceased donors. This study includes pancreatic islets from 3 donors. The experiments were approved by the Regional Ethical Review Boards in Uppsala and in Stockholm.

Islet Transplantation

Mice were fasted overnight and then injected with 150 mg/kg of streptozotocin (Sigma-Aldrich) via intraperitoneal injection. When the glucose level was >300 mg/dl, 0.2 U/kg/day of insulin (Eli Lilly & Co.) was injected to maintain glycemia. Islets were isolated from donor mice and 100 islets were transplanted into the anterior chamber of the eye of the recipient mouse (Speier et al., 2008).

Electrophysiological Recordings

Adenovirus infected single islet cells were subjected to conventional whole-cell patch-clamp analysis with an EPC-10 patch clamp amplifier (HEKA Elektronik, Lambrecht/Pfalz, Germany). The cells were bathed in the external solution (138 mM NaCl, 10 mM TEACl, 10 mM $CaCl_2$, 5.6 mM KCl, 1.2 mM $MgCl_2$, 5 mM HEPES, 3 mM glucose, pH 7.4). Borosilicate glass electrodes (1.2 mm outside diameter;

Warner Instrument, Hamden, Conn.) were pulled with a vertical pipette puller (PC-10; Narishige, Tokyo, Japan), and the recording pipette had tip resistances ranging between 2 and 3 MΩ when filled with pipette solution (150 mM N-methy-D-glucamine, 2 mM CaCl2, 10 mM EGTA, 1 mM MgCl$_2$, 5 mM HEPES, 20 mM ATP, pH7.2). All recordings were performed at room temperature. The amplitude of whole-cell Ca$^{2+}$ currents was normalized to cell capacitance. Acquisition and analysis of data were done using Patchmaster (HEKA Elektronik).

Statistics

All results are presented as means±SEM. An unpaired Student's t-test was used for pairwise comparisons. Statistical significance of results from glucose and insulin tolerance tests were assessed by two-way repeated-measures ANOVA followed by multiple comparison with Bonferroni's correction. A p-value<0.05 was considered statistically significant.

I claim:

1. A method for treating or limiting the development of diabetes, comprising transplanting into the eye of a subject with diabetes or at risk of developing diabetes an amount of insulin-producing cells engineered to reduce expression of a β3 subunit of Cav (voltage-gated calcium channel) (CavB3) that is effective for treating or limiting the development of the diabetes, wherein the reduced expression level is relative to a normal control.

2. The method of claim 1, wherein the insulin-producing cells are engineered to disrupt each copy of the Cavβ3 gene.

3. The method of claim 1, wherein the insulin-producing cells are further engineered to reduce expression of the apoCIII gene.

4. The method of claim 3, wherein the insulin-producing cells are engineered to disrupt each copy of the apoCIII gene.

5. The method of claim 1, wherein the insulin-producing cells are further engineered to reduce expression of one or more chemokine genes, selected from the group consisting of CCL2, CCL3, CCLS, CXCL1, CXCL9, CXCL10, CXCL11, and a combination thereof, and/or one or more cytokine genes, selected from the group consisting of IL-6, IL-8 and the combination thereof.

6. The method of claim 5, wherein the insulin-producing cells are engineered to disrupt each copy of the one or more chemokine genes and/or the one or more cytokine genes.

7. The method of claim 1, wherein the insulin-producing cells are further engineered to reduce expression of one or more major histocompatibility complex (MHC) class I proteins.

8. The method of claim 7, wherein the insulin-producing cells are engineered to disrupt each copy of the one or more MHC class I proteins.

9. The method of claim 1, wherein the insulin-producing cells are further engineered to increase expression of one or more proteins beneficial to insulin producing cells, wherein the beneficial proteins are selected from the group consisting of GLP1 receptors, insulin receptors, cytokine IL1B, and a combination thereof.

10. The method of claim 1, wherein the insulin-producing cells comprise isolated pancreatic islets or isolated pancreatic β cells.

11. The method of claim 1, wherein the transplantation into the eye involves transplantation into the anterior chamber of the eye.

12. The method of claim 11, wherein the transplantation into the anterior chamber of the eye involves injection through the cornea.

13. The method of claim 1, wherein the subject has diabetes and the amount of the insulin-producing cells that have a reduced expression of the β3 subunit of Cav transplanted is effective for treating the diabetes.

14. The method of claim 1, wherein the subject has type 2 diabetes.

15. The method of claim 14, wherein the subject has type 1 diabetes.

16. The method of claim 1, wherein the subject is at risk of developing diabetes and the amount of the insulin-producing cells that have a reduced expression of the β3 subunit of Cav transplanted is effective for limiting the development of the diabetes.

17. The method of claim 16, wherein the subject is at risk of type 2 diabetes.

18. The method of claim 16, wherein the subject is at risk of type 1 diabetes.

19. The method of claim 1, wherein the subject overexpresses Cavβ3 compared to a normal control.

20. The method of claim 1, wherein the subject is human.

* * * * *